United States Patent [19]

Chambers et al.

[11] Patent Number: 4,760,089
[45] Date of Patent: Jul. 26, 1988

[54] IRREVERSIBLE DOPAMINE-β-HYDROXYLASE INHIBITORS

[75] Inventors: Pamela A. Chambers, St. Davids, Pa.; James S. Frazee, Collingswood, N.J.; Carl Kaiser, Haddon Heights, N.J.; Lawrence I. Kruse, Haddonfield, N.J.

[73] Assignee: SmithKline Beckman Corporation, Philadelphia, Pa.

[21] Appl. No.: 773,694

[22] Filed: Sep. 9, 1985

[51] Int. Cl.⁴ .................. A01K 31/275; C07C 121/80
[52] U.S. Cl. .................................. 514/523; 558/406; 558/408; 560/55; 568/441
[58] Field of Search .................. 560/55; 568/441; 514/523; 558/406, 408

[56] References Cited

PUBLICATIONS

Taguchi et al., "Chem. Pharm. Bult.", vol. 29, No. 1 (1981), pp. 55-62.
Eiden et al., Arch. Pharmaz., 306, pp. 470-475 (1973).
Eiden et al., Arch. Pharmaz., 304, pp. 628-633 (1971).
Temulis et al., Chem. Abstracts, vol. 85: 123138p (1976).

Primary Examiner—Anton H. Sutto
Attorney, Agent, or Firm—Vincent L. Fabiano; Stuart R. Suter; Alan D. Lourie

[57] ABSTRACT

Potent, irreversible dopamine-β-hydroxylase inhibitors having the Formula:

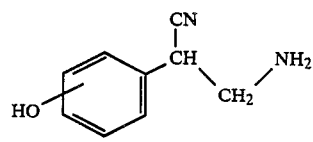

which are useful to inhibit dopamine-β-hydroxylase activity, pharmaceutical compositions including these inhibitors or 2-cyano-2-phenethylamine, and methods of using these inhibitors or 2-cyano-2-phenethylamine to inhibit dopamine-β-hydroxylase activity in mammals. Also disclosed are novel intermediates useful in preparing the presently invented inhibitors.

17 Claims, 1 Drawing Sheet

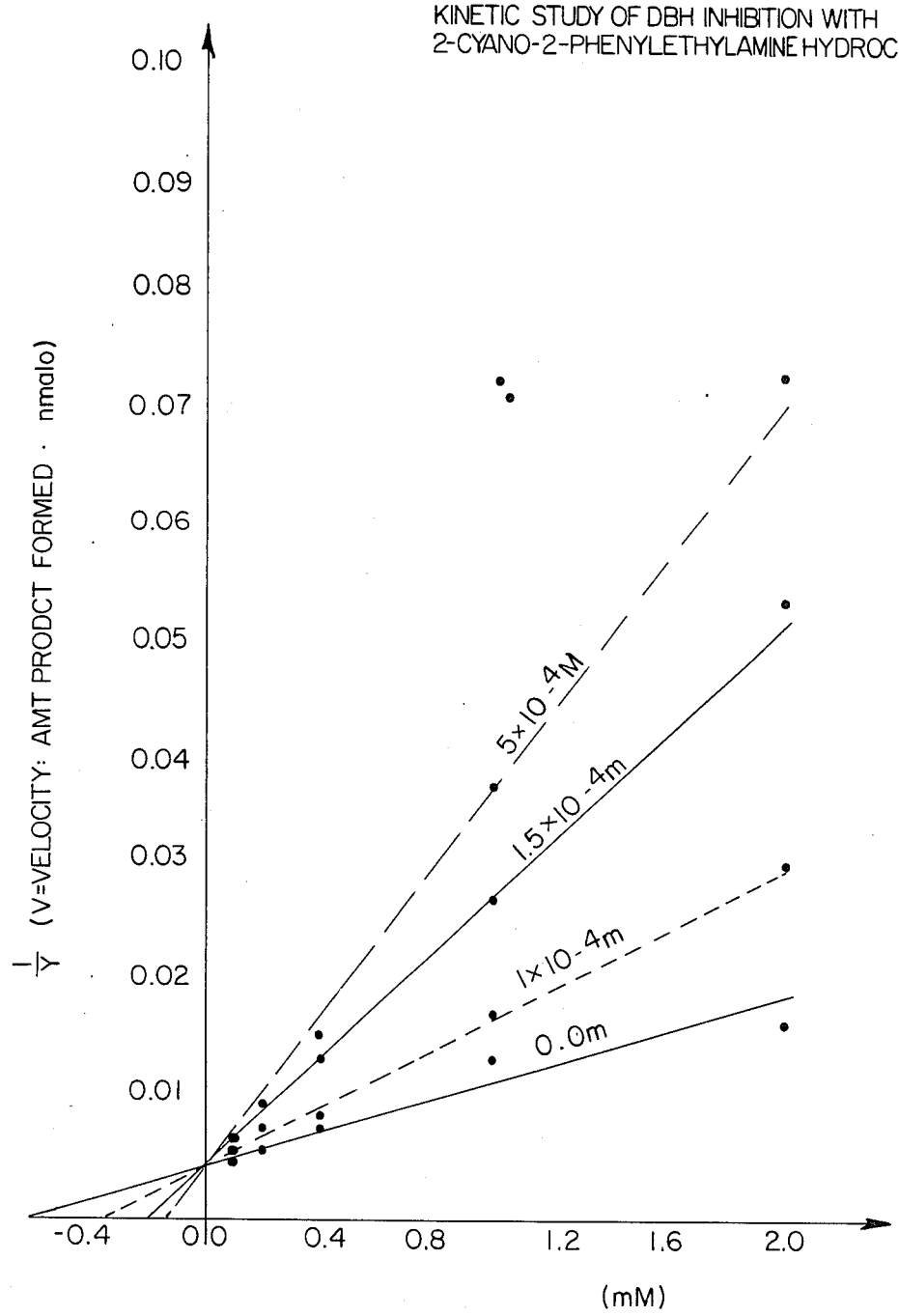

IRREVERSIBLE DOPAMINE-β-HYDROXYLASE INHIBITORS

FIELD OF THE INVENTION

This invention relates to novel compounds that irreversibly inhibit dopamine-β-hydroxylase, novel pharmaceutical compositions and methods of inhibiting dopamine-β-hydroxylase.

BACKGROUND OF THE INVENTION

In the catecholamine biosynthetic pathway, tyrosine is converted in three steps to norephinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of reversible DBH inhibitors are known. These generally are divided into two classes, namely, metal chelating agents, which bind to copper in the enzyme, and phenethylamine analogues. Rosenberg et al., "Essays in Neurochemistry and Neuropharmacology," Vol. 4, edit. by Youdim et al., John Wiley & Sons, 1980, pp. 179–192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6- carbon side chain on a phenethylamine analogue may yield potent inhibitors.

Known reversible DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See, Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci.* 107, 878 (1963)].

Each of the above compounds except benzyloxyamine and benzylhydrazine apparently owes its inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoyl)methylpicolinic acid are DBH inhibitors.

Bupicomide, 5-(n-butyl)picolinamine, is reported by Ehrreich et al., "New Antihypertensive Drugs", Spectrum Publications, 1976, pg. 409–432, to be a DBH inhibitor that possesses the ability to lower blood pressure.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

Friedman et al., *Psychosomatic Med.* 40, 107 (1978), report that patients treated with alpha-methyl-DOPA, guanethidine, and reserpine, but not propranolol and diuretics, have lowered DBH levels, although the significance of the observation is uncertain.

Non-specific, often toxic effects of known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

Previously disclosed has been the following compound:

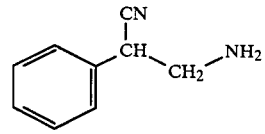

Eiden and Swan, in two reports, have described a synthetic method for this compound and have described the use of this compound in chemical reaction mechanism studies. Acyl enamines. 24. 1-acyl-3-aza-1,4-pentadienes. *Arch. Pharm.* 306:470–75 (1973); Acyl enamines. 21. Reactions of 1-phenyl-1-cyano-2 aminoethylene with substituted acetaldehydes, *Arch. Pharm.*

304:628–33 (1971). This compound also has been used in studies of the physical properties of related compounds. Temulis, A, et al., The Electronic Structure and Spectral Characteristics of α-Substituted Acrylonitriles, Chem. Abstr. 85:123138p. Absent from these reports is any indication that this compound inhibits DBH or has any pharmacologic activity.

SUMMARY OF THE INVENTION

The present invention resides in the discovery that DBH is inhibited by substituted 2-cyanophenethylamine compounds and that the DBH inhibition produced by these compounds is irreversible. These compounds are potent and produce prolonged DBH inhibition.

Presently preferred compounds of the invention include:

2-cyano-2-(m-hydroxyphenyl)ethylamine.

In a further aspect of the invention there are provided novel intermediates useful in preparing hydroxy substituted 2-cyanophenethylamine compounds. Each of the intermediates is the p-methoxybenzyloxy analogue of a substituted hydroxybenzene.

The invention also is a method of inhibiting DBH activity in mammals, including humans, which comprises administering internally to a subject an effective amount of 2-cyano-2-phenethylamine or a 2-cyano-2-(hydroxyphenyl)ethylamine compound.

Included in the present invention are pharmaceutical compositions comprising compounds useful in the method of the invention and a pharmaceutical carrier.

BRIEF DESCRIPTION OF THE DRAWING

FIG. 1 is a double-reciprocal plot of DBH activity in the presence of several concentrations of 2-cyano-2-phenylethylamine.

DETAILED DESCRIPTION OF THE INVENTION

The presently invented compounds that irreversibly inhibit DBH have the following formula:

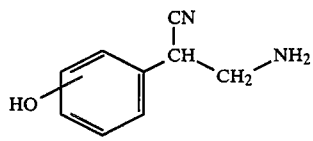

or a pharmaceutically acceptable salt or hydrate thereof.

Compounds of Formula I and the compound related to those of Formula I, except that the hydroxy group is replaced by hydrogen, were prepared from benzalmalonate or a p-methoxybenzyloxybenzalmalonate by known processes such as shown in Scheme I, below. Benzalmalonate is known and described in published references and can be obtained readily. Starting p-methoxybenzyloxy benzalmalonates are prepared from p-methoxybenzyl alcohols as described in Scheme II, below.

Scheme I illustrates reaction of benzalmalonates (A) having a substituent Q which is p-methoxybenzyloxy or hydrogen with potassium cyanide to form corresponding 3-cyano-3-phenyl or substituted phenyl propionic acids (B). Upon reaction with p-methoxybenzyl alcohol, diphenylphosphorylazide, and triethylamine, the 3-cyano-3-phenyl or substituted phenyl propionic acids (B) yield p-methoxybenzyl carbamates of 2-cyano-2-phenyl or substituted phenylethylamines (C). The carbamates (C) then are hydrolyzed with hydrogen chloride in diethyl ether to produce hydrochloric acid salts of 2-cyano-2-phenyl or substituted phenylethylamines (D) in which W is hydrogen or hydroxy. Treatment of those carbamates (C) in which Q is p-methoxybenzyloxy with hydrogen chloride in diethyl ether also cleaves the p-methoxybenzyl moiety to yield hydrogen chloride salts of 2-cyano-2-(hydroxyphenyl)ethylamines (D). The free 2-cyano-2-(hydroxyphenyl)ethylamines are prepared by treatment of the hydrogen chloride salts of 2-cyano-2-(hydroxyphenyl)ethylamines (D) with a base such as ammonium hydroxide in an appropriate solvent.

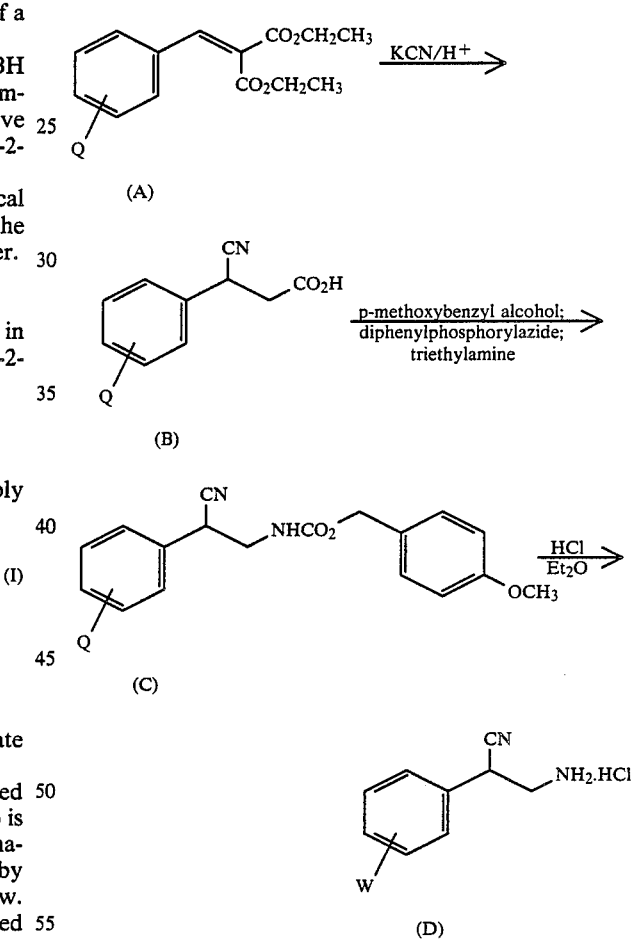

Q is p-methoxybenzyloxy or hydrogen
W is hydroxy or hydrogen

A process for preparing p-methoxybenzyloxy benzalmalonates and for using these compounds in synthesizing 2-cyano-2-(hydroxyphenyl)ethylamines was devised and employed in the preparation of the presently invented 2-cyano-2-(hydroxyphenyl)ethylamines. In producing 2-cyano-2-(hydroxyphenyl)ethylamines by the devised synthetic process, novel intermediates of the following formula were synthesized:

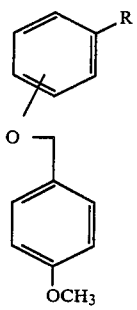

in which: R is

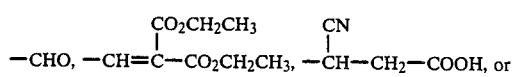

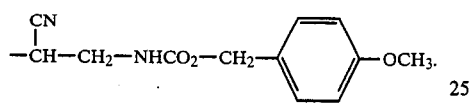

The devised synthetic process is depicted in Scheme II. A known compound, p-methoxybenzyl alcohol (J) is the starting material for this process. Initially, p-methoxybenyzl alcohol (J) is reacted with concentrated hydrochloric acid to yield p-methoxybenzyl chloride (K). p-Methoxybenzyloxy substituted benzaldehydes (L) then are produced by reaction of p-methoxybenzyl-chloride (K) with an appropriate hydroxybenzaldehyde dissolved in a suitable solvent such as dimethylformamide. Condensation of the p-methoxybenzyloxy substituted benzaldehyde (L) with diethylmalonate in a suitable solvent such as toluene containing an appropriate catalyst such as piperidine yields p-methoxybenzyloxy substituted benzalmalonates which are included in the compounds of formula (A) in Scheme I. The p-methoxybenzyloxy substituted benzalmalonates (A) thus formed thereafter are utilized as starting materials in Scheme I, above, to produce the 2-cyano-2-(hydroxyphenyl)ethylamines of the present invention which are included in compounds of formula (D) in Scheme I.

Scheme II

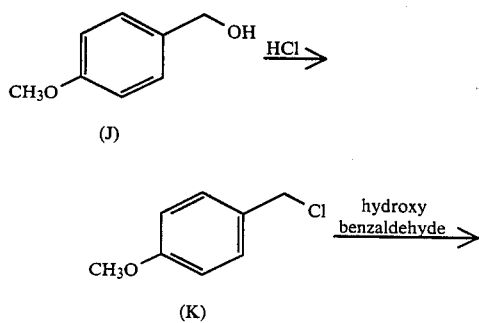

-continued
Scheme II

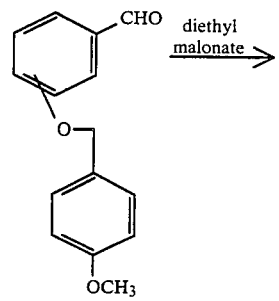

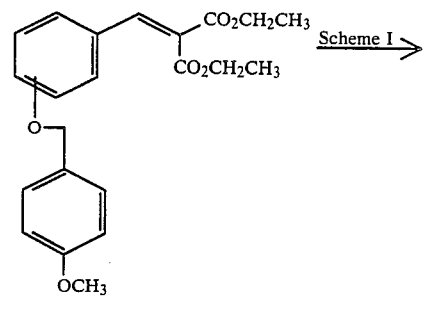

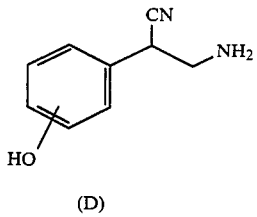

The pharmaceutically acceptable acid addition salts of the compounds of the invention are formed with strong or moderately strong organic or inorganic acids by methods known in the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Presently invented also are methods of producing DBH inhibition in mammals, including humans, by administering an effective amount of 2-cyano-2-phenethylamine or a 2-cyano-2-(hydroxyphenyl)ethylamine compound. In vitro enzyme inhibition kinetic studies demonstrate that the compounds useful in the method of the invention are potent DBH inhibitors. DBH activity was assayed by a standard procedure for measuring the conversion of tyramine to octopamine in the presence of DBH. J. J. Pisano, et al., *Biochim. Biophy.* Acta, 43, 566–68 (1960). Octopamine was assayed following sodium periodate oxidation to p-hydroxybenzaldehyde by measuring spectrophotometric absorbance at 330 nm.

As the data shown in FIG. 1 demonstrate, reductions in DBH activity were related directly to increasing 2-cyano-2-phenethylamine hydrochloride concentrations. Further, the changing apparent rate constant and the unchanging maxiumum reaction rate indicate that the compounds useful in the presently invented method initially are competitive blockers of substrate-enzyme interactions.

Although the kinetic data indicate that 2-cyano-2-phenethylamine and 2-cyano-2-(hydroxyphenyl)ethylamines competitively inhibit enzymatic conversion of substrate, it was demonstrated that these compounds are irreversible inhibitors of DBH. Dialysis of enzyme-inhibitor complexes was selected as the approach for testing the reversibility of the inhibition produced by these compounds. A known, reversible DBH inhibitor, fusaric acid, was utilized as a reference standard. Following approximate 3 hour incubation of DBH with one of the inhibitors, the rate of enzymatic conversion of tyramine to octopamine was measured by the standard procedure used in the enzyme kinetic analyses. Thereafter, the enzyme previously incubated with inhibitor was placed in a standard dialysis bag and dialyzed overnight against four changes of pH 5.5 acetate buffer. Following dialysis, the rate of enzymatic conversion of tyramine to octopamine again was measured.

TABLE I

| Incubated with DBH | Amount of Product Formed | | DBH Activity | |
|---|---|---|---|---|
| | Pre-Dialysis | Post-Dialysis | Pre-Dialysis | Post-Dialysis |
| Tyramine ($10^{-2}$ M) | 196.0 nM | 190.5 nM | 100% | 100% |
| Tyramine ($10^{-2}$ M) and Fusaric Acid ($10^{-4}$ M) | 4.0 nM | 169.0 nM | 2.0% | 89.2% |
| Tyramine ($10^{-2}$ M) and 2-cyano-2-phenethylamine hydrochloride ($10^{-3}$ M) | 15.7 nM | 10.5 nM | 8.0% | 5.5% |

The data shown in Table 1 demonstrate that the DBH inhibition produced by 2-cyano-2-phenyl and 2-hydroxyphenylethylamine compounds is irreversible. Under the dialysis conditions employed, it is expected that all non-covalently bound substances complexed with DBH were removed. Thus, these data also suggest that the mechanism of the irreversible DBH inhibition involves covalent binding of enzyme-activated inhibitor to the enzyme.

One of the 2-cyano-2-phenethylamine compounds also was tested for its effect in vivo on peripheral dopamine (DA) and norepinephrine (NE) levels substantially by the procedure of DaPrada and Zurcher, *Life Sciences*, 19, 1161, (1976). Groups of five spontaneously hypertensive rats were dosed orally, twice, the second dose approximately 18 hours after the first, and were sacrificed about 2 hours after the second dose. Averaged results, expressed in micrograms of DA and NE per gram of tissue are given in Table II.

TABLE II

| Compound | DA ($\mu$g/g) | NE($\mu$g/g) | DA/NE Ratio |
|---|---|---|---|
| Experiment 1 | | | |
| Control (Saline) | 0.468 ± | 9.75 ± | 0.0470 ± 0.004 |
| | 0.059 | 0.627 | |
| Fusaric Acid 50 mg/kg | 0.819 ± 0.047* | 8.31 ± 0.492 | 0.0994 ± 0.007* |
| 2-cyano-2-phenethylamine hydrochloride 100 mg/kg | 0.571 ± 0.042 | 7.96 ± 0.315* | 0.0716 ± 0.004* |
| Experiment 2 | | | |
| Control (Saline) | 0.309 ± 0.017 | 7.66 ± 0.194 | 0.0406 ± .0031 |
| Fusaric Acid 50 mg/kg | 0.615 ± 0.034* | 5.82 ± 0.211* | 0.112 ± 0.0055* |
| 2-cyano-2-phenethylamine hydrochloride 100 mg/kg | 0.408 ± 0.036* | 6.47 ± 0.487 | 0.0628 ± 0.0013* |

*$p < 0.05$

Further, spontaneously hypertensive rats were dosed with a suspension or solution of 2-cyano-2-phenethylamine hydrochloride at a dose of 100 mg/kg intraperitoneally, and mean arterial blood pressure was monitored for 260 minutes using indwelling cannulae positioned in the tail arteries. Approximate thirty percent reductions in blood pressure were observed thirty to forty minutes following administration of this compound. At 260 minutes after administration of this compound, blood pressure remained reduced by approximately twenty percent when compared to vehicle-treated controls.

The compounds useful in the methods of this invention can be incorporated into convenient dosage forms such as capsules, tablets or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds in a pharmaceutical dosage unit will be an efficacious, nontoxic quantity selected from the range of 0.1–1,000 mg/kg of active compound, preferably 10–100 mg/kg. The selected dose is administered orally, rectally, or by injection from one to six times daily, or continuously by infusion to a human patient in need of treatment. Parenteral administration, which uses lower dosages, is preferred. Oral administration, at higher dosages, however, also can be used when safe and convenient for the patient.

The following examples are illustrative of preparation of 2-cyano-2-phenethylamine hydrochloride and Formula I compounds. Example 2 illustrates preparation of the novel intermediates. The examples are not intended to limit the scope of the invention as defined hereinabove and as claimed below. All temperatures and melting points (mp) are given in degrees Celsius (°C.).

EXAMPLE 1

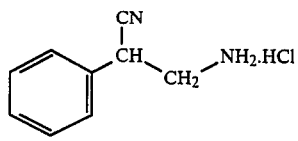

(i) Preparation of 3-cyano-3-phenyl propionic acid

A solution of benzalmalonate (124 g., 0.5 mole) in ethanol (560 ml.) and water (240 ml.) was heated at reflux for 60 hours with potassium cyanide (45 g., 0.7 mole). The solution was cooled, concentrated to remove ethanol, and then acidified with concentrated hydrochloric acid. The product was extracted with dichloromethane, and the extracts were washed with brine, dried over anhydrous sodium sulfate, and concentrated. The residue was dissolved in ethyl acetate (500 ml.) and treated with dicyclohexylamine (82 ml.) to yield 118 g. (67%) of white crystals which were collected by filtration and washed sequentially with ethyl acetate and ether and dried. A suitable cation-exchange resin in the acid form, such as Dowex ® 50x8-100 ion-exchange resin, (20 g.) was washed with acetone and suspended in methanol (130 ml.) with dicyclohexylammonium salt (15 g.). After stirring at ambient temperature for 1 hour, the cation exchange resin was removed by filtration and the filtrate was concentrated to yield 3-cyano-3-phenylpropionic acid as an oil.

(ii) Preparation of N-p-methoxybenzyloxycarbonyl-2-cyano-2-phenethylamine

3-Cyano-3-phenylpropionic acid (5.8 g., 0.033 mole), diphenylphosphorylazide (9.1 g., 0.033 mole), triethylamine (3.3 g., 0.033 mole), and p-methoxybenzyl alcohol (4.8 g., 0.035 mole) were dissolved in 100 ml. of dry toluene and heated at 100° for 12 hours. The solvent was stripped and water was added to the residue. Following extraction with ether, the ether layer was washed well with water and dried over anhydrous magnesium sulfate. The crude product then was chromatographed (flash column chromatography, Baker silica gel-10 μm particule size, 2:1 hexane/ethyl acetate eluant) to yield 5.3 g. of 2-cyano-2-phenethylamine-N-p-methoxybenzyloxycarbonyl.

(iii) Preparation of 2-cyano-2-phenethylamine hydrochloride

2-Cyano-2-phenethylamine-N-p-methoxybenzyloxycarbonyl (9.8 g.) was dissolved in 100 ml. of ether. Diethyl ether saturated with hydrogen chloride (45 ml.) was added and the reaction was stirred for 2 hours at room temperature, and then allowed to stand overnight. The precipitated product was collected, washed with ether and recrystallized from methanol/ethyl acetate to yield 3.2 g. of 2-cyano-2-phenethylamine hydrochloride, m.p. 183°-185° C.

EXAMPLE 2

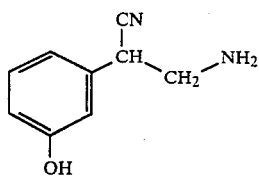

(i) Preparation of p-methoxybenzylchloride p-Methoxybenzyl alcohol (34.5 g., 0.25 mole) was added to 100 ml. of concentrated hydrochloric acid. The mixture was stirred at ambient temperature for 1 hour, then poured into ice water. The product was extracted with ether. The ether solution was washed well with 5% sodium bicarbonate, then with water and dried over anhydrous magnesium sulfate to yield 32.1 g. of p-methoxybenzyl chloride.

(ii) Preparation of 3-(p-methoxybenzyloxy)benzaldehyde m-Hydroxybenzaldehyde (24.1 g., 0.197 mole) was dissolved in 150 ml. of dimethylformamide. To this solution were added p-methoxybenzyl chloride (9.5 g., 0.197 mole) and 50% sodium hydride (in mineral oil) in small portions at room temperature. The reaction was stirred under an argon atmosphere for 2 hours, then allowed to stand overnight. The reaction mixture was poured into a large volume of ice water. The product 3-(p-methoxybenzyloxy)benzaldehyde was collected and recrystallized from ethanol; 42.9 g., mp 78° C.

(iii) Preparation of 3-(p-methoxybenzyloxy)benzylidenemalonic acid diethyl ester 3-(p-Methoxybenzyloxy)benzaldehyde (24.2 g., 0.10 mole) and diethyl malonate (16 g., 0.10 mole) were dissolved in 60 ml. toluene containing 0.6 ml. of piperidine and 2 ml. of glacial acetic acid. The reaction was refluxed until the water ceased to collect in the Dean-Stark trap. The cooled reaction was diluted with ethyl acetate. This solution was washed with 5% sodium bicarbonate, then washed once with water and dried over anhydrous magnesium sulfate. The crude product was chromatographed (flash column chromatography, Baker silica gel 40 μm particle size, 3:1 hexane/ethyl acetate eluant) to yield 25.9 g. of 3-(p-methoxybenzyloxy)benzylidenemalonic acid diethyl ester as a viscous oil.

(iv) Preparation of 3-cyano-3-[3'-(p-methoxybenzyloxy)phenyl]propionic acid 3-(p-methoxybenzyloxy)benzylidene malonic acid diethyl ester (13.3 g., 0.035 mole) and potassium cyanide (3.2 g., 0.049 mole) were heated together in 90 ml. of 70:30 ethanol:water for 60 hours. The solvent was stripped and the residue carefully acidified with 7 ml. concentrated hydrochloric acid. Water (100 ml.) was added and the product was extracted with ethyl acetate. The ethyl acetate extract was washed well with water and dried over anhydrous magnesium sulfate. Dicyclohexylamine (6.3 g., 0.035 mole) was added. If no precipitation of the dicyclohexylamine salt occurred, the solvent was stripped and the residue triturated with acetonitrile. The salt was collected and recrystallized from methanol/acetonitrile to yield 11.9 g. of product; m.p. 142°-145° C.

The dicyclohexylamine salt then was dissolved in 130 ml. of methanol. A cation exchange resin in the acid form (Dowex ® 50x8-100, 20 g.) was prewashed with acetone and added to the methanol solution of the dicyclohexylamine salt to form a slurry. This slurry was stirred for 1 hour. The resin was removed by filtration and the solvent stripped to yield 7.5 g. of 3-cyano-3-[3'-(p-methoxybenzyloxy)phenyl]propionic acid.

(v) Preparation of N-p-methoxybenzyloxycarbonyl-2-cyano-2-[3''-(p-methoxybenzyloxy)phenyl]ethylamine 3-Cyano-3-[3'-(p-methoxybenzyloxy)phenyl]propionic acid (10.2 g., 0.033 mole), diphenylphosphorylazide (9.1 g., 0.033 mole), triethylamine (3.3 g., 0.033 mole), and p-methoxybenzyl alcohol (4.8 g., 0.035 mole) were dissolved in 100 ml. of dry toluene and heated at 100° for 12 hours. The solvent was stripped and water was added to the residue. Following extraction with ether, the ether layer was washed well with water and dried over anhydrous magnesium sulfate. The crude product then was chromatographed (flash column chromatography, Baker silica gel-10 μm particle size, 2:1 hexane/ethyl acetate eluant) to yield 8.9 g. of N-p-methoxybenzyloxycarbonyl-2-cyano-2-[3'-(p-methoxybenzyloxy)-phenyl]ethylamine.

(iv) Preparation of 2-cyano-2-(3'-hydroxylphenyl)ethylamine

N-p-Methoxybenzyloxycarbonyl-2-cyano-2-(3'-hydroxyphenyl)ethylamine (8.9 g.) was dissolved in 100 ml. ether. Diethyl ether saturated with hydrogen chloride (45 ml.) was added and the reaction was stirred for 2 hours at room temperature, and then allowed to stand overnight. The precipitated product was collected, washed with ether and recrystallized from methanol/ethyl acetate to yield 1.3 g. of 2-cyano-2-(3'-hydroxyphenyl)ethylamine hydrochloride, m.p. 164°–166° C.

The free base, 2-cyano-2-(3'-hydroxyphenyl)ethylamine, was prepared by treating an aqueous ethanolic solution of the hydrochloric acid salt with ammonium hydroxide. The free base was extracted with diethyl ether. Evaporation of the ether yields 2-cyano-2-(3'-hydroxyphenyl)ethylamine.

EXAMPLE 3

An oral dosage form for administering the presently invented compounds is produced by screening, mixing, and filling into a hard gelatin capsule the ingredients in Table III, below.

TABLE III

| Ingredients | Amounts |
|---|---|
| 2-cyano-2-phenethylamine hydrochloride | 50 mg |
| magnesium stearate | 5 mg |
| lactose | 75 mg |

EXAMPLE 4

The sucrose, calcium sulfate dihydrate and 2-cyano-2-(hydroxyphenyl)ethylamine shown in Table IV below, are mixed and granulated with a 10% gelatin solution. The wet granules are screened, dried, mixed with the starch, talc and stearic acid, screened and compressed into a tablet.

TABLE IV

| Ingredients | Amounts |
|---|---|
| 2-cyano-2-(3'-hydroxyphenyl)ethylamine | 100 mg |
| calcium sulfate dihydrate | 150 mg |
| sucrose | 20 mg |
| starch | 10 mg |
| talc | 5 mg |
| stearic acid | 3 mg |

EXAMPLE 5

2-Cyano-2-(3'-hydroxyphenyl)ethylamine hydrochloride, 75 mg., is dispursed in 25 ml. of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of the Formula:

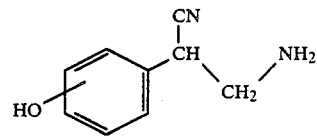

or a pharmaceutically acceptable salt or hydrate thereof.

2. The compound of claim 1 that is: 2-cyano-2-(3'-hydroxyphenyl)ethylamine.

3. The compound of claim 1 that is: 2-cyano-2-(3'-hydroxyphenyl)ethylamine hydrochloride.

4. A pharmaceutical composition for inhibiting dopamine-β-hydroxylase activity, comprising a pharmaceutically acceptable carrier and an amount sufficient to produce said inhibition of a compound of the Formula:

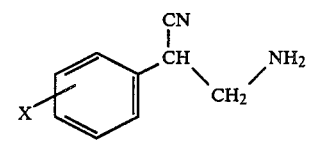

in which:
X is hydrogen or hydroxy; or a pharmaceutically acceptable salt or hydrate thereof.

5. The pharmaceutical composition of claim 4, in which the compound is 2-cyano-2-phenethylamine.

6. The pharmaceutical composition of claim 4, in which the compound is 2-cyano-2-phenethylamine hydrochloride.

7. The pharmaceutical composition of claim 4, in which the compound is 2-cyano-2-(3'-hydroxyphenyl)ethylamine.

8. The pharmaceutical composition of claim 4, in which the compound is 2-cyano-2-(3'-hydroxyphenyl)ethylamine hydrochloride.

9. A method of inhibiting dopamine-β-hydroxylase activity in mammals which comprises administering internally to a subject in need of the inhibition an effective amount of a compound of the Formula:

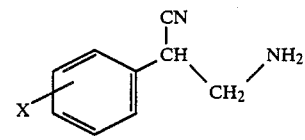

in which:
X is hydrogen or hydroxy; or a pharmaceutically acceptable salt or hydrate thereof.

10. The method of claim 9 in which the compound is 2-cyano-2-phenethylamine.

11. The method of claim 9 in which the compound is 2-cyano-2-phenethylamine hydrochloride.

12. The method of claim 9 in which the compound is 2-cyano-2-(3'-hydroxyphenyl)ethylamine.

13. The method of claim 9 in which the compound is 2-cyano-2-(3'-hydroxyphenyl)ethylamine hydrochloride.

14. A compound having the Formula:

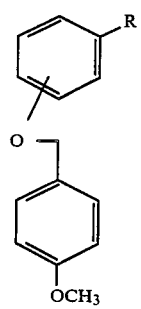

in which:
R is

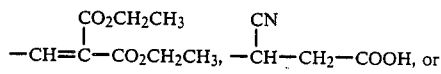

15. The compound of claim 14 in which R is

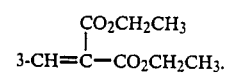

16. The compound of claim 14 in which R is

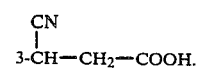

17. The compound of claim 14 in which R is

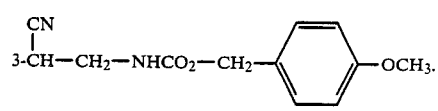

* * * * *